(12) United States Patent
Mabande et al.

(10) Patent No.: US 9,091,433 B2
(45) Date of Patent: Jul. 28, 2015

(54) MONOLITH CATALYST AND USE THEREOF

(75) Inventors: Godwind Tafara Peter Mabande, Limburgerhof (DE); Soo Yin Chin, Mannheim (DE); Goetz-Peter Schindler, Ludwigshafen (DE); Gerald Koermer, Basking Ridge, NJ (US); Dieter Harms, Bad Nenndorf (DE); Burkhard Rabe, Husum (DE); Howard Furbeck, Hamilton, NJ (US); Oliver Seel, Nienburg (DE)

(73) Assignee: BASF SE (DE)

( * ) Notice: Subject to any disclaimer, the term of this patent is extended or adjusted under 35 U.S.C. 154(b) by 192 days.

(21) Appl. No.: 13/321,388

(22) PCT Filed: May 18, 2010

(86) PCT No.: PCT/EP2010/056769
§ 371 (c)(1),
(2), (4) Date: Nov. 18, 2011

(87) PCT Pub. No.: WO2010/133565
PCT Pub. Date: Nov. 25, 2010

(65) Prior Publication Data
US 2012/0065443 A1 Mar. 15, 2012

Related U.S. Application Data

(60) Provisional application No. 61/179,918, filed on May 20, 2009.

(51) Int. Cl.
| | | |
|---|---|---|
| *F23C 13/08* | (2006.01) | |
| *B01J 19/24* | (2006.01) | |
| *B01J 23/40* | (2006.01) | |
| *B01J 23/42* | (2006.01) | |
| *B01J 23/58* | (2006.01) | |
| *B01J 23/62* | (2006.01) | |
| *B01J 23/63* | (2006.01) | |
| *B01J 23/656* | (2006.01) | |
| *B01J 23/96* | (2006.01) | |
| *B01J 35/00* | (2006.01) | |
| *B01J 35/02* | (2006.01) | |
| *B01J 35/04* | (2006.01) | |
| *B01J 37/00* | (2006.01) | |
| *B01J 37/02* | (2006.01) | |
| *C07C 5/333* | (2006.01) | |
| *C07C 5/393* | (2006.01) | |
| *B01J 21/04* | (2006.01) | |
| *B01J 21/06* | (2006.01) | |
| *B01J 38/10* | (2006.01) | |
| *B01J 38/12* | (2006.01) | |

(52) U.S. Cl.
CPC ............. *F23C 13/08* (2013.01); *B01J 19/2485* (2013.01); *B01J 21/066* (2013.01); *B01J 23/40* (2013.01); *B01J 23/42* (2013.01); *B01J 23/58* (2013.01); *B01J 23/624* (2013.01); *B01J 23/63* (2013.01); *B01J 23/6567* (2013.01); *B01J 23/96* (2013.01); *B01J 35/002* (2013.01); *B01J 35/0026* (2013.01); *B01J 35/023* (2013.01); *B01J 35/04* (2013.01); *B01J 37/0036* (2013.01); *B01J 37/0045* (2013.01); *B01J 37/0205* (2013.01); *B01J 37/0228* (2013.01); *B01J 37/0242* (2013.01); *B01J 37/0248* (2013.01); *C07C 5/3337* (2013.01); *C07C 5/393* (2013.01); *B01J 21/04* (2013.01); *B01J 21/06* (2013.01); *B01J 38/10* (2013.01); *B01J 38/12* (2013.01); *C07C 2523/42* (2013.01); *C07C 2523/62* (2013.01); *F23C 2900/9901* (2013.01)

(58) Field of Classification Search
None
See application file for complete search history.

(56) References Cited

U.S. PATENT DOCUMENTS

| | | | |
|---|---|---|---|
| 3,449,461 A | 6/1969 | Jenkins | |
| 3,670,044 A * | 6/1972 | Drehman et al. | 585/433 |
| 4,755,359 A | 7/1988 | Klatt et al. | |
| 4,762,960 A * | 8/1988 | Imai | 585/660 |
| 4,788,371 A | 11/1988 | Imai et al. | |
| 5,207,053 A * | 5/1993 | Spadaccini et al. | 60/780 |
| 5,525,570 A | 6/1996 | Chakraborty et al. | |
| 5,733,518 A * | 3/1998 | Durante et al. | 423/248 |
| 6,166,283 A * | 12/2000 | Bharadwaj et al. | 585/658 |
| 6,365,543 B1 | 4/2002 | Schmidt et al. | |
| 6,486,370 B1 * | 11/2002 | Rende et al. | 585/444 |
| 7,087,802 B2 * | 8/2006 | Schindler et al. | 585/660 |

(Continued)

FOREIGN PATENT DOCUMENTS

| | | |
|---|---|---|
| CA | 1305123 C | 7/1992 |
| CA | 2 429 492 A1 | 5/2002 |

(Continued)

OTHER PUBLICATIONS

Emmet, Paul H., "Alkylation, Isomerization, Polymerization, Cracking and Hydroreforming", Catalysis, vol. 6, (1958), pp. 535-542.

*Primary Examiner* — Walter D Griffin
*Assistant Examiner* — Jelitza Perez
(74) *Attorney, Agent, or Firm* — Drinker Biddle & Reath LLP

(57) ABSTRACT

The invention relates to a catalyst comprising a monolith composed of a catalytically inert material with low BET surface area and a catalyst layer which has been applied to the monolith and comprises, on an oxidic support material, at least one noble metal selected from the group consisting of the noble metals of group VIII of the Periodic Table of the Elements, optionally tin and/or rhenium, and optionally further metals, wherein the thickness of the catalyst layer is 5 to 500 micrometers.

12 Claims, No Drawings

(56) References Cited

U.S. PATENT DOCUMENTS

| | | | |
|---|---|---|---|
| 2004/0015031 A1* | 1/2004 | Messenger | 585/658 |
| 2004/0030214 A1 | 2/2004 | Schindler et al. | |
| 2004/0034266 A1 | 2/2004 | Brophy et al. | |
| 2004/0044261 A1 | 3/2004 | Feng et al. | |
| 2006/0004241 A1 | 1/2006 | Schindler et al. | |
| 2007/0207078 A1 | 9/2007 | Nochi et al. | |
| 2008/0177117 A1 | 7/2008 | Benderly et al. | |

FOREIGN PATENT DOCUMENTS

| | | |
|---|---|---|
| CN | 1479649 A | 3/2004 |
| DE | 195 00 366 C1 | 5/1996 |
| DE | 197 27 021 A1 | 1/1999 |
| EP | 0 838 534 A1 | 4/1998 |
| EP | 0878443 A1 | 11/1998 |
| EP | 1757364 A1 | 2/2007 |
| EP | 1842591 A1 | 10/2007 |
| JP | S61-197032 A | 9/1986 |
| JP | S61-291039 A | 12/1986 |
| JP | 2005-539034 A | 12/2005 |
| JP | 2007-216137 A | 8/2007 |
| JP | 2007-530260 A | 11/2007 |
| JP | 2008-110974 A | 5/2008 |
| WO | WO-94/29021 A1 | 12/1994 |
| WO | WO-96/33150 A1 | 10/1996 |
| WO | WO-96/33151 A1 | 10/1996 |
| WO | WO-00/14180 A1 | 3/2000 |
| WO | WO-2006/036193 A1 | 4/2006 |
| WO | WO-2007/111997 A2 | 10/2007 |
| WO | WO-2009/118593 A1 | 10/2009 |

* cited by examiner

MONOLITH CATALYST AND USE THEREOF

CROSS-REFERENCE TO RELATED APPLICATIONS

This application is a national stage application (under 35 U.S.C. §371) of PCT/EP2010/056769, filed May 18, 2010, which claims benefit of U.S. Provisional Application No. 61/179,918, filed May 20, 2009.

BACKGROUND OF THE INVENTION

The invention relates to a monolith catalyst and to the use thereof for petrochemical conversions such as dehydrogenations, aromatizations, reformings and combustions.

In numerous petrochemical reactions (for example dehydrogenations, aromatizations, reformings and combustions), supported noble metal catalysts are used. The use of such catalysts is very expensive owing to high noble metal costs. In addition, unfavorable noble metal distribution and long diffusion pathways in conventional catalysts lead to low noble metal exploitation.

U.S. Pat. No. 4,788,371 describes a process for steam dehydrogenation of dehydrogenatable hydrocarbons in the gas phase combined with oxidative reheating of the intermediates, with the same catalyst being used for the selective oxidation of hydrogen and the steam dehydrogenation. Here, hydrogen can be introduced as co-feed. The catalyst used comprises a noble metal of group VIII, an alkali metal and a further metal selected from the group consisting of B, Ga, In, Ge, Sn and Pb on an inorganic oxide support such as aluminum oxide. The process can be carried out in one or more stages in a fixed or moving bed.

WO 94/29021 describes a catalyst which comprises a support consisting essentially of a mixed oxide of magnesium and aluminum Mg(Al)O and also a noble metal of group VIII, preferably platinum, a metal of group IVA, preferably tin, and possibly an alkali metal, preferably cesium. The catalyst is used in the dehydrogenation of hydrocarbons, which can be carried out in the presence of oxygen.

U.S. Pat. No. 5,733,518 describes a process for the selective oxidation of hydrogen by oxygen in the presence of hydrocarbons such as n-butane over a catalyst comprising a phosphate of germanium, tin, lead, arsenic, antimony or bismuth, preferably tin. The combustion of the hydrogen generates, in at least one reaction zone, the heat of reaction necessary for the endothermic dehydrogenation.

EP-A 0 838 534 describes a catalyst for the steam-free hydrogenation of alkanes, in particular isobutane, in the presence of oxygen. The catalyst used comprises a platinum group metal applied to a support comprising tin oxide/zirconium oxide and having a tin content of at least 10%. The oxygen content of the feed stream for the dehydrogenation is calculated so that the quantity of heat generated by the combustion reaction of hydrogen and oxygen is equal to the quantity of heat required for the dehydrogenation.

WO 96/33151 describes a process for the dehydrogenation of a $C_2$-$C_5$-alkane in the absence of oxygen over a dehydrogenation catalyst comprising Cr, Mo, Ga, Zn or a group VIII metal with simultaneous oxidation of the resulting hydrogen over a reducible metal oxide, e.g. an oxide of Bi, In, Sb, Zn, Tl, Pb or Te. The dehydrogenation has to be interrupted at regular intervals in order to reoxidize the reduced oxide by means of an oxygen source. U.S. Pat. No. 5,430,209 describes a corresponding process in which the dehydrogenation step and the oxidation step proceed sequentially and the associated catalysts are separated physically from one another. Catalysts used for the selective oxidation of hydrogen are oxides of Bi, Sb and Te and also their mixed oxides.

Finally, WO 96/33150 describes a process in which a $C_2$-$C_5$ alkane is dehydrogenated over a dehydrogenation catalyst in a first stage, the output gas from the dehydrogenation stage is mixed with oxygen and, in a second stage, passed over an oxidation catalyst, preferably $Bi_2O_3$, so as to selectively oxidize the hydrogen formed to water, and, in a third stage, the output gas from the second stage is again passed over a dehydrogenation catalyst.

It is known that aromatic hydrocarbons can be obtained by catalytic dehydrogenating aromatization of open-chain hydrocarbons (see, for example, Catalysis VI, p. 535-542, ed. by P. H. Emmet, Reinhold Publishing Co., New York, 1958).

U.S. Pat. No. 3,449,461 describes the dehydrogenating aromatization of open-chain $C_6$ to $C_{20}$ paraffins to aromatic hydrocarbons including o-xylene with the aid of a sulfur catalyst which comprises a noble metal such as palladium or platinum.

US-A 2004/0044261 describes a process for selectively preparing p-xylene by converting $C_8$ isoalkenes or alkenes over a catalyst which comprises a molecular sieve laden with a noble metal of transition group VIII.

DE-A 197 27 021 describes a process for preparing $C_8$ aromatics from butenes by dehydrogenating olefinically unsaturated $C_8$ hydrocarbon mixtures obtainable by dimerizing technical $C_4$ cuts over a catalyst which comprises at least one element of the platinum group on an amphoteric ceramic support. The main reaction product is ethylbenzene; in addition, o-xylene is also formed.

DETAILED DESCRIPTION OF THE INVENTION

It is an object of the present invention to provide a process for the dehydrogenation of hydrocarbons which ensures high conversions, space-time yields and selectivities.

The object is achieved by a catalyst comprising a monolith composed of a catalytically inert material with low BET surface area and a catalyst layer which has been applied to the monolith and comprises, on an oxidic support material, at least one noble metal selected from the group consisting of the noble metals of group VIII of the Periodic Table of the Elements, optionally tin and/or rhenium, and optionally further metals, wherein the thickness of the catalyst layer is 5 to 500 micrometers.

The invention provides fixed bed catalysts with a significantly lowered noble metal requirement and improved performance. At the same time, the penetration depth of the catalyst is limited to 5 to 500 μm, preferably 5 to 250 μm, more preferably 25 to 250 μm and especially 50 to 250 μm. The penetration depth of the catalyst is limited by the thickness of the catalyst layer applied to the monolith.

The catalyst layer on the monolith comprises at least a ceramic oxide as catalyst support and at least a noble metal selected from the elements of transition group VIII of the Periodic Table of the Elements, especially palladium, platinum or rhodium, optionally rhenium and/or tin. The catalyst support are one or more ceramic oxides of elements from the second, third and fourth main group and the third and fourth transition group (group IVB) of the elements and of the lanthanides, especially MgO, CaO, $Al_2O_3$, $SiO_2$, $ZrO_2$, $TiO_2$, $La_2O_3$ and $Ce_2O_3$. In a particularly preferred embodiment, the catalyst support comprises $SiO_2$ and $ZrO_2$, in particular a mixed oxide of $SiO_2$ and $ZrO_2$.

In addition to the noble metals of transition group VIII, it is possible to use further elements; in particular, rhenium and/or tin should be understood as additions to the elements of transition group VIII. Another constituent is the addition of or the doping with either compounds of the third main or transition group (IIIA or IIIB) or basic compounds such as alkali earths, alkaline earths or rare earths, or their compounds which can be converted to the corresponding oxides at temperatures above 400° C. Simultaneous doping with a plurality of the elements mentioned or their compounds is possible. Suitable examples are potassium and lanthanum compounds. In addition, the catalyst may be admixed with sulfur, tellurium, arsenic, antimony or selenium compounds, which in many cases bring about an increase in the selectivity, presumably by partial "poisoning" (moderators).

The catalyst layer comprises at least one noble metal from group VIII of the Periodic Table of the Elements (Ru, Rh, Pd, Os, Ir, Pt). The preferred noble metal is platinum. The catalyst layer may optionally comprise tin and/or rhenium; it preferably comprises tin.

In a preferred embodiment, the catalyst layer comprises platinum and tin.

In addition, the catalyst layer may be doped with further metals. In a preferred embodiment, the catalyst layer comprises one or more metals of the third transition group (group IIIB) of the Periodic Table of the Elements including the lanthanides (Sc, Y, La, Ce, Pr, Nd, Sm, Eu, Gd, Tb, Dy, Ho, Er, Tm, Yb, Lu), preference being given to cerium and lanthanum, particular preference to lanthanum.

In a further preferred embodiment, the catalyst layer comprises platinum, tin and lanthanum.

In addition, the catalyst layer may comprise metals selected from the metals of main groups I and II of the Periodic Table of the Elements. In a preferred embodiment, the catalyst layer comprises potassium and/or cesium. In a specific embodiment, the catalyst layer comprises platinum, tin, lanthanum and an alkali metal selected from the group consisting of potassium and cesium.

The catalyst layer comprising the oxidic support material and the at least one noble metal of group VIII of the Periodic Table of the Elements, tin and/or rhenium and if appropriate further metals is applied to the monolith by washcoating the catalytically active material. For this purpose, it is alternatively also possible first to apply a catalyst support layer composed of oxidic support material to the monolith by washcoating and to impregnate this layer in a later process step with one or more different solutions comprising the metals.

The inventive catalysts are used especially for the dehydrogenation of alkanes to alkenes, for example of propane to propene or of n-butane to butenes (1- and 2-butene), for dehydrogenating aromatization and for the catalytic combustion of hydrogen with oxygen.

Monoliths

Suitable monolithic structures are either metal or ceramic. Preferably, they consist of single blocks with small (0.5-4 mm) parallel channels. Preferably monolith parts from either Corning Incorporated or NGK or Denso are used.

The most common material for monolithic structures is cordierite (a ceramic material consisting of magnesia, silica, and alumina in the ratio of 2:5:2). Other materials whose monolith structures are commercially available are metals, mullite (mixed oxide of silica and alumina, ratio 2:3) and silicon carbide. These materials have, similar to cordierite, a low Brunauer, Emmet, and Teller (BET) specific surface area (e.g., for cordierite, typically 0.7 m$^2$/g). A low BET surface area in the context with this invention is a BET surface area of <10 m$^2$/g.

Preferably monolith parts of cordierite are used according to the invention.

Ceramic monolithic elements are available with cell densities of 25-1600 cpsi (cells per square inch, equal to a cell size of 5-0.6 mm). By using a higher cell density, the geometrical surface area increases and, thus, the catalyst can be used more effectively. Disadvantages of higher cell densities are a somewhat more difficult manufacturing process, more difficult washcoating, and a higher pressure drop over the reactor. However, the pressure drop remains very low for high-cell-density monoliths (typically a factor of 10 lower) compared to a packed-bed reactor, because of the straight monolith channels.

Preferably, cell densities of monolithic elements used according to the present invention are from 100 to 1200 cpsi, most preferably 300 to 600 cpsi.

Ceramic monolithic elements can be prepared by preparing a mixture of talc, clay, and an alumina-yielding component and silica, mixing the mixture to form a moldable composition, molding the mixture, drying the greenware, and heating it at a temperature of 1200 to 1500° C. to form a ceramic containing mainly cordierite and having a low coefficient of thermal expansion. Generally speaking, a paste with appropriate rheological properties and composition can be extruded into a monolith support. The paste usually consists of a mixture of ceramic powders of suitable sizes, inorganic and/or organic additives, solvent (water), peptizer (acid) to adjust pH, and a permanent binder (colloidal solution or a sol). The additives can be a plasticizer or a surfactant to adjust the viscosity of the paste, or a temporary binder, which can be burned off later. Sometimes, glass or carbon fibers are added to enhance the mechanical strength of the monolith. The permanent binder should improve the integrity of the monolith.

Cordierit monoliths can be produced from a batch consisting of talc, kaolin, calcined kaolin, and alumina that collectively provide a chemical compound of $SiO_2$ 45 to 55, $Al_2O_3$ 32 to 40, and MgO 12 to 15 wt %. Talc is a material mainly consisting of hydrous magnesium silicate, $Mg_3Si_4O_{10}(OH)_2$. Depending on the source and purity of the talc, it may also be associated with other minerals such as tremolite ($CaMg_3(SiO_3)_4$), serpentine ($3MgO \cdot 2SiO_2, 2H_2O$), anthophyllite ($Mg_7(OH)_2(Si_4O_{11})_2$), magnesite ($MgCO_3$), mica, and chlorite.

Extrusion can also be used to produce monoliths of other materials such as SiC, $B_4C$, $Si_3N_4$, BN, AlN, $Al_2O_3$, $ZrO_2$, mullite, Al titanate, $ZrB_2$, sialon, perovskite, carbon and $TiO_2$.

In extrusion, in addition to the quality of the die and the nature and the properties of the materials used to make the moldable mixture, the additives added, pH, water content, and the force used in extrusion are also of importance with respect to the properties of the monolith products. The additives applied in extrusion are, for example, celluloses, $CaCl_2$, ethylene, glycols, diethylene glycols, alcohols, wax, paraffin, acids and heat-resistant inorganic fibers. Besides water, other solvents can also be used such as ketones, alcohols, and ethers. The addition of additives may lead to improved properties of the monoliths such as the production of microcracks that enhances the resistance to thermal shock, better porosity and absorbability, and enhanced mechanical strength or a low thermal expansion.

Washcoating Procedure

According to the present invention, the bare monolithic structure is coated with a catalyst support layer comprising one or more ceramic oxides or a catalyst layer comprising the catalytically active metals and the optional further (promoter)

elements already supported on the ceramic oxide support material, wherein the coating is produced by a washcoating procedure.

The macroporous structure of ceramic monoliths facilitates the anchoring of the washcoat layer. The manner in which washcoating is carried out can be divided into two methods: the macroporous support can be (partly) filled with the high-surface-area washcoat material, or a washcoat can be deposited as a layer in the pores on the ceramic support. Pore filling results in the strongest interaction between monolith and washcoat, as most of the coat layer is actually fixated inside the pores of the support instead of only being attached to the external surface of the monolith channels. This type of coating is carried out by using a solution (or sol) of the material to be deposited or by using a solution containing very small colloidal particles. The disadvantage of coating by means of pore filling is that the amount of coating that can be deposited is limited, because at one stage, pores will be completely filled and the washcoat will become inaccessible.

Preferably, the catalyst support or catalyst layer is coated on the monolithic walls. Coating a layer on the monolith walls has the advantages that higher loadings are possible and that diffusion into the thicker walls does not influence the reaction. This type of coating is carried out by coating with a suspension of particles of similar size as the macropores in the monolith walls, e.g. cordierite (typically 5 μm). The principle by which the slurry-coating procedures operate is the following. The monolith is placed in the liquid containing suspended particles. The pores in the wall take up liquid, depositing the particles on the monolith walls, because the particles cannot enter the pores, leaving a layer of deposited particles.

A washcoating solution or slurry is prepared in which a dried monolith is immersed for a short period (dipped). Preferably, the pre-dried and evacuated piece of monolith is dipped into the sol or slurry. The monolith is removed from the liquid and most liquid is shaken out, the remainder being gently blown out by pressurized air. Most commonly, this is done by using an "air-knife", a thin slit blowing pressurized air, because, in this manner, a complete row of channels is cleared simultaneously. The monolith is then dried in the horizontal position, being rotated continuously around its axis, to prevent gravity from causing an uneven washcoat distribution. Finally, the coating is fixated to the monolith by a high-temperature calcination step. The washcoat loading obtained is typically 5-10 wt % for most methods. If a higher loading is required, the coating procedure should be repeated. This can be done after calcinations or the monolith can be dipped again after drying.

To prepare the catalyst support layer, the monolith can be washcoated with a suitable sol. The sol can be prepared via a hydrolytic route. One method for the preparation of a sol is hydrolysis of an appropriate alkoxide. The hydrolysis of metal alkoxide is usually accelerated by the presence of an acid or a base. During aging of the sol, a polycondensation process proceeds, leading to crosslinking and the formation of polymer-like compounds.

In one embodiment of the present invention, the monolithic structure is washcoated with alumina using an Al sol. In addition to alkoxide hydrolysis mentioned above, an Al sol can be prepared from other Al precursors, e.g. from pseudo-boehmite $AlO(OH), xH_2O$ or from hydrolysis of $AlCl_3$.

Additives, e.g. urea or organic amines such as hexamethylenetetramine, can be added to the sol in order to improve the quality of alumina obtained. Moreover, the additives may influence the stability of the sols.

Optionally, cations, e.g., La, Mg, Zr, Si, which inhibit the transition of active alumina into the inert α-phase, can be incorporated in the sol in order to stabilize the washcoated alumina against sintering upon heat treatment.

In a further embodiment of the present invention, the monolithic structure is washcoated with silica using a Si sol. Si sol can be prepared from hydrolysis of tetraalkoxysilicate (TAOS), tetramethoxysilicate (TMOS), tetraethoxysilicate (TEOS), and tetrapropoxysilicate (TPOS). Due to the fact that the TAOS are usually immiscible with water, alcohols are often added as a cosolvent to obtain a homogeneous sol.

Other oxides can be washcoated similarly. When mixed sols are used in washcoating, a mixed oxidic layer may be formed on the monolith surface.

Silica can be coated easily using commercial colloidal silica solutions, e.g., of the Ludox AS type. Water glass can be added to enhance the integrity of the silica coating. The silica colloidal solutions can also be used as a permanent binder for coating zeolites and other materials, e.g., titania and zirconia or a resin catalyst. The washcoating can be carried out analogously to the procedures described above for alumina washcoating.

It is also possible to washcoat metallic monoliths with or without a prior oxidation. In the former case, the adhesion of the washcoat layer is better.

Instead of a sol, a slurry can be used in order to prepare the catalyst support layer or catalyst layer. This can increase the amount of oxide coated each time. Moreover, optimized catalyst powders can be used in the washcoating to prepare monolithic catalysts. Often ballmilling for a certain period is necessary to reduce the size of the solid particles to a certain size to favor the coating.

In a preferred embodiment of the invention, the particle size of the oxidic support material is reduced by milling to an average size of from 1 to 40 μm, preferably from 5 to 20 μm. The given average particle size is defined as encompassing 90% of the particles.

The active component, which is usually a metal of transition group VIII, is generally applied by impregnation with a suitable metal salt precursor. Instead of impregnation, the active component can also be applied by other methods, for example spraying the metal salt precursor onto the support. Suitable metal salt precursors are, for example, the nitrates, acetates and chlorides of the corresponding metals; it is also possible to use hydroxides or complex anions of the metals used. Preference is given to using platinum as $H_2PtCl_6$ or $Pt(NO_3)_2$. Suitable solvents for the metal salt precursors include both water and organic solvents. Particularly useful solvents are water and lower alcohols such as methanol and ethanol.

To apply alkali metals and alkaline earth metals, use is advantageously made of aqueous solutions of compounds which can be converted into the corresponding oxides by calcination. Suitable compounds are, for example, hydroxides, carbonates, oxalates, acetates or basic carbonates of the alkali metals and alkaline earth metals. If the catalyst support is doped with metals of main or transition group III, use is frequently made of the hydroxides, carbonates, nitrates, acetates, formates or oxalates which can be converted into the corresponding oxides by calcination, for example $La(OH)_3$, $La_2(CO_3)_2$, $La(NO_3)_3$, lanthanum acetate, lanthanum formate or lanthanum oxalate.

In one preferred embodiment of the present invention, post-impregnation of the active components after washcoating and calcining a monolitic honeycomb is carried out as follows:

The raw materials, i.e. the support material(s) and—if needed—the binder for a stable washcoat, are mixed in an appropriate vessel, container etc. and stirred or kneaded when suspended with water. The resulting slurry is diluted to the required total solid content and adjusted to defined pH using defined acids and bases. Then, the slurry is pumped through a continuous mill for particle size reduction to an average size of from 1 to 40 µm, preferably from 5 to 20 µm; the particle size distribution can be controlled off-line by laser diffraction. The resulting slurry is used for coating.

Coating can be done for example manually by using a hand nozzle for an air ducted process. The right total solid content for the coating can be determined in a targeting procedure to achieve the defined washcoat loading in g/in$^3$ or g/L.

The parts are immersed lengthwise preferably to 80-90% but not fully into the slurry and—after taking them out—are turned so that the slurry drains through the cells. The final washcoat loading is determined by using the air gun to distribute the slurry across the channel and to blow out excessive amounts of slurry. The coating steps may be repeated to achieve the targeted total washcoat loading. The prototypes are dried after each coating step at from 100 to 200° C., preferably at from 120 to 140° C. and calcined at from 400 to 750° C., preferably from 550 to 650° C. prior to the next step.

The thickness of the layer is defined by the targeted total amount of applied washcoat deriving from the density of the washcoat ingredients and their particle size distribution. Depending on the rheology of the suspension the total amount of the washcoat has to be applied in more than one coating step.

For impregnation of the active components the water uptake is determined with a representative prototype. The active components are dissolved in the right concentration in water and the part is drowned into this solution for a defined amount of time, mostly some seconds, then the excessive amount of water is blown off with an air nozzle. These impregnation steps are repeated as often as required by the recipe. After each impregnation step the prototypes can be dried and calcined as described above.

In an alternative embodiment, the active components are already impregnated into the support material(s) and/or added to the slurry prior to or after milling. Adjustments for the total solid content or pH are preformed as described above. The coating steps may have to be repeated to achieve the targeted total washcoat loading. The prototypes can be dried after each coating step at from 100 to 200° C., preferably at from 120 to 140° C. and calcined at from 400 to 750° C., preferably from 550 to 650° C. prior to the next step.

The penetration depth ($d_{WC}$) can be determined from the washcoat loading (WCL), the washcoat density ($\rho_{WC}$) and the geometric surface area (GSA) of the monolith:

$$d_{WC} = \frac{WCL/\rho_{WC}}{GSA}$$

The washcoat density ($\rho_{WC}$) can be determined from the densities of the finished monolith catalyst ($\rho_{catalyst}$) and of the substrate ($\rho_{substrate}$), substrate)) and the washcoat loading and the specific weight (SW: volume-based total weight of the catalyst) of the monolith catalyst:

$$\rho_{WC} = \frac{WCL}{SW/\rho_{catalyst} - (SW - WC)/\rho_{substrate}}$$

The densities of the monolith catalyst and of the substrate can be determined by means of mercury or helium density measurements.

Catalysts for Dehydrogenating Aromatization and Dehydrogenation which are Applied as Layer on the Monoliths To prepare a catalyst layer suitable for the dehydrogenating aromatization and dehydrogenation, so-called amphoteric ceramic oxides, i.e. in particular oxides of zirconium and of titanium or mixtures thereof, can be used; also suitable are corresponding compounds which can be converted to these oxides by calcining. They can be prepared by known processes, for example by the sol-gel process, precipitation of the salts, dewatering of the corresponding acids, dry mixing, slurrying or spray-drying.

Suitable ceramic support oxides are all modifications of zirconium oxide and titanium oxide. However, it has been found to be advantageous for the preparation of catalysts on the basis of $ZrO_2$ when the proportion of monoclinic $ZrO_2$ detectable by X-ray diffraction is more than 90%. Monoclinic $ZrO_2$ is characterized in the X-ray diffractogram by two strong signals in the two-theta range of about 28.2 and 31.5.

The doping with a basic compound can be effected during the preparation, for example by coprecipitation, or subsequently, for example by impregnating the ceramic oxide with an alkali metal or alkaline earth metal compound or a compound of an element of the third transition group or a rare earth metal compound.

The content of alkali metal or alkaline earth metal, metal of main or transition group III, rare earth metal or zinc is generally up to 20% by weight, preferably between 0.1 and 15% by weight, more preferably between 0.1 and 10% by weight. The alkali metal and alkaline earth metal providers used are generally compounds which can be converted to the corresponding oxides by calcining. Suitable examples are hydroxides, carbonates, oxalates, acetates, nitrates or mixed hydroxycarbonates, or alkali metals and alkaline earth metals.

When the ceramic support is doped additionally with a metal of the third main or transition group, the starting materials in this case too should be compounds which can be converted to the corresponding oxides by calcining. When lanthanum is used, for example, lanthanum compounds which comprise organic anions, such as lanthanum acetate, lanthanum formate or lanthanum oxalate, are suitable.

The noble metal constituents may be applied in different ways. For example, the ceramic catalyst support material or the catalyst support layer on the monolith can be impregnated or sprayed with a solution of a corresponding compound of the noble metal, or of rhenium or tin. Suitable metal salts for preparing such solutions are, for example, the nitrates, halides, formates, oxalates, acetates of the noble metal compounds. It is also possible to use complex anions, or acids of these complex anions, such as $H_2PtCl_6$. Particularly suitable compounds for preparing the inventive catalysts have been found to be $PdCl_2$, $Pd(OAc)_2$, $Pd(NO_3)_2$ and $Pt(NO_3)_2$.

Noble metal sols with one or more components in which the active component is already present completely or partly in the reduced state can also be used.

When noble metal sols are used, these are prepared beforehand in a customary manner, for example by reduction of a metal salt or of a mixture of a plurality of metal salts in the presence of a stabilizer such as polyvinylpyrrolidone, and then applied to it either by impregnating or spraying the ceramic catalyst support material or the catalyst catalyst support layer. The preparation technique is disclosed in the German patent application 1 95 00 366.7.

The content in the catalyst of elements of transition group VIII and optionally rhenium or tin may, for example, be from 0.005 to 5% by weight, preferably from 0.01 to 2% by weight, more preferably from 0.05 to 1.5% by weight. When rhenium or tin is used in addition, its ratio to the noble metal constituent may, for example, be from 0.1:1 to 20:1, preferably from 1:1 to 10:1.

The moderating additives used (according to the common conception of partial poisoning of the catalyst) may, if required, be compounds of sulfur, of tellurium, of arsenic or of selenium. The addition of carbon monoxide during the operation of the catalyst is also possible. The use of sulfur has been found to be particularly advantageous, which is conveniently applied in the form of ammonium sulfide, $(NH_4)_2S$. The molar ratio of noble metal components to moderating compound may be from 1:0 to 1:10, preferably from 1:1 to 1:0.05.

The catalyst material generally has a BET surface area of up to 500 $m^2/g$, usually from 2 to 300 $m^2/g$, more preferably from 5 to 300 $m^2/g$. The pore volume is generally between 0.1 and 1 ml/g, preferably from 0.15 to 0.6 ml/g, more preferably from 0.2 to 0.4 ml/g. The mean pore diameter of the mesopores determinable by Hg penetration analysis is generally between 8 and 60 nm, preferably between 10 and 40 nm. The proportion of the pores having a width of more than 20 nm varies generally between 0 and 90%; it has been found to be advantageous to use supports having a macropore fraction (i.e. pores of width more than 20 nm) of more than 10%.

One example for a dehydrogenating aromatization for which the catalysts of the invention can be used is the dehydrogenating aromatization of 3,4- or 2,3-dimethylhexene to o-Xylene.

In one embodiment of the invention the catalyst material forming the catalyst layer on the monolith has a bimodal pore radius distribution and comprises a) from 10 to 99.9% by weight of zirconium dioxide and
b) from 0 to 60% by weight of aluminum oxide, silicon oxide and/or titanium oxide and
c) from 0.1 to 30% by weight of at least one element of main group I or II, of an element of transition group III including cerium and lanthanum, of an noble metal of transition group VIII of the Periodic Table of the Elements, and optionally tin, with the proviso that the sum of the percentages by weight is 100. This catalyst material is in particular suitable for the dehydrogenation of alkanes to alkenes and the dehydrogenating aromatization, e.g. from 3,4- or 2,3-dimethylhexene to o-Xylene.

This catalyst material forming the catalyst layer on the monolith preferably comprises a) from 10 to 99.9% by weight, more preferably from 20 to 98% by weight, particularly preferably from 30 to 95% by weight, of zirconium dioxide of which from 50 to 100% by weight, preferably from 60 to 99% by weight, particularly preferably from 70 to 98% by weight, is in the monoclinic and/or tetragonal modification and
b) from 0.1 to 60% by weight, preferably from 0.1 to 50% by weight, particularly preferably from 1 to 40% by weight, in particular from 5 to 30% by weight, of aluminum oxide, silicon dioxide and/or titanium dioxide in the form of rutile or anatase, and
c) from 0.1 to 10% by weight, preferably from 0.1 to 8% by weight, particularly preferably from 0.1 to 5% by weight, of at least one element selected from main group I or II, transition groups III and VIII and from the transition group of the Periodic Table of the Elements, cerium, lanthanum and/or tin, where the sum of the percentages by weight is 100.

In one particularly preferred embodiment, component b) consists of from 0.1 to 30% by weight, preferably from 0.5 to 25% by weight, particularly preferably from 1 to 20% by weight of silicon dioxide.

The catalyst material preferably consists of the composition as specified above.

The catalyst material forming the catalyst layer on the monolith comprises from 70 to 100%, preferably from 75 to 98%, particularly preferably from 80 to 95%, of larger pores than 20 nm, preferably between 40 and 5000 nm.

To produce the catalyst material forming the catalyst layer on the monolith, use can be made of precursors of the oxides of zirconium, titanium, lanthanum, cerium, silicon and aluminum (forming the support) which can be converted by calcination into the oxides. These can be prepared by known methods, for example by the sol-gel process, precipitation of the salts, dehydration of the corresponding acids, dry mixing, slurrying or spray drying. For example, a $ZrO_2.xAl_2O_3.xSiO_2$ mixed oxide can be prepared by first preparing a water-rich zirconium oxide of the general formula $ZrO_2.xH_2O$ by precipitation of a suitable zirconium-containing precursor. Suitable zirconium precursors are, for example, $Zr(NO_3)_4$, $ZrOCl_2$ or $ZrCl_4$. The precipitation itself is carried out by addition of a base such as NaOH, $Na_2CO_3$ and $NH_3$ and is described, for example, in EP-A 849 224.

To prepare a $ZrO_2.xSiO_2$ mixed oxide, the Zr precursor obtained as above can be mixed with an Si-containing precursor. Well suited $SiO_2$ precursors are, for example, water-containing sols of $SiO_2$ such as Ludox®. The two components can be mixed, for example, by simple mechanical mixing or by spray drying in a spray tower.

When using mixed oxides, it is possible to influence the pore structure in a targeted way. The particle sizes of the various precursors influence the pore structure. Thus, for example, macropores can be generated in the microstructure by use of $Al_2O_3$ having a low loss on ignition and a defined particle size distribution. An aluminum oxide which has been found to be useful for this purpose is Puralox ($Al_2O_3$ having a loss on ignition of about 3%).

To prepare a $ZrO_2.xSiO_2.xAl_2O_3$ mixed oxide, the $SiO_2.xZrO_2$ powder mixture obtained as described above can be admixed with an Al-containing precursor. This can be carried out, for example, by simple mechanical mixing in a kneader. However, a $ZrO_2.xSiO_2.xAl_2O_3$ mixed oxide can also be prepared in a single step by dry mixing of the individual precursors.

A further possible way of producing the support having a specific pore radius distribution for the catalysts mentioned, in a targeted manner, is to add, during the preparation, various polymers which can be partly or completely removed by calcination so as to form pores in defined pore radius ranges. The mixing of the polymers and the oxide precursors can, for example, be carried out by simple mechanical mixing or by spray drying in a spray tower.

The use of PVP (polyvinylpyrrolidone) has been found to be particularly advantageous for producing the supports having a bimodal pore radius distribution. If PVP is added during a production step to one or more oxide precursors of the elements Zr, Ti, La, Ce, Al or Si, macropores in the range from 200 to 5000 nm are formed after calcination. A further advantage of the use of PVP is that the support can be shaped more readily. Thus, extrudates having good mechanical properties can be produced from freshly precipitated water-containing $ZrO_2.xH_2O$ which has previously been dried at 120° C. when PVP and formic acid are added, even without further oxide precursors.

The mixed oxide supports of the catalysts generally have higher BET surface areas after calcination than do pure $ZrO_2$ supports. The BET surface areas of the mixed oxide supports are generally from 40 to 300 m$^2$/g, preferably from 50 to 200 m$^2$/g, particularly preferably from 60 to 150 m$^2$/g. The pore volume of the catalysts of the present invention used is usually from 0.1 to 0.8 ml/g, preferably from 0.2 to 0.6 ml/g. The mean pore diameter of the catalysts of the present invention, which can be determined by Hg porosimetry, is from 5 to 30 nm, preferably from 8 to 25 nm. Furthermore, it is advantageous for from 10 to 80% of the pore volume to be made up by pores >40 nm.

The calcination of the mixed oxide supports is advantageously carried out after the application of the active components and is carried out at from 400 to 750° C., preferably from 500 to 700° C., particularly preferably from 550 to 650° C. The calcination temperature should usually be at least as high as the reaction temperature of the dehydrogenation.

The catalyst material has a bimodal pore radius distribution. The pores are mostly in the range up to 20 nm and in the range from 40 to 5000 nm. Based on the pore volume, these pores make up at least 70% of the pores. The proportion of pores less than 20 nm is generally from 20 to 60%, while the proportion of pores in the range from 40 to 5000 nm is generally likewise from 20 to 60%.

The doping of the mixed oxides with a basic compound can be carried out either during their preparation, for example by coprecipitation, or subsequently, for example by impregnation of the mixed oxide with an alkali metal compound or alkaline earth metal compound or a compound of transition group III or a rare earth metal compound. Particularly suitable dopants are K, Cs and La.

The application of the dehydrogenation-active component, which is a noble metal of transition group VIII, is generally carried out by impregnation with a suitable metal salt precursor which can be converted into the corresponding metal oxide by calcination. As an alternative to impregnation, the dehydrogenation-active component can also be applied by other methods, for example spraying the metal salt precursor onto the support. Suitable metal salt precursors are, for example, the nitrates, acetates and chlorides of the appropriate metals, or complex anions of the metals used. Preference is given to using platinum as $H_2PtCl_6$ or $Pt(NO_3)_2$. Solvents which can be used for the metal salt precursors are water and organic solvents. Particularly suitable solvents are lower alcohols such as methanol and ethanol.

Further suitable precursors when using noble metals as dehydrogenation-active component are the corresponding noble metal sols which can be prepared by one of the known methods, for example by reduction of a metal salt with a reducing agent in the presence of a stabilizer such as PVP. The preparation technique is dealt with comprehensively, for example in the German Patent Application DE-A 195 00 366.

As alkali metal and alkaline earth metal precursors, use is generally made of compounds which can be converted into the corresponding oxides by calcination. Examples of suitable precursors are hydroxides, carbonates, oxalates, acetates or mixed hydroxycarbonates of the alkali metals and alkaline earth metals.

If the mixed oxide support is additionally or exclusively doped with a metal of main group III or transition group III, the starting materials in this case too should be compounds which can be converted into the corresponding oxides by calcination. If lanthanum is used, suitable starting compounds are, for example, lanthanum oxide carbonate, $La(OH)_3$, $La_2(CO_3)_3$, $La(NO_3)_3$ or lanthanum compounds containing organic anions, e.g. lanthanum acetate, lanthanum formate or lanthanum oxalate.

Dehydrogenation Catalysts which are Applied as Layers on the Monoliths

Further suitable dehydrogenation catalyst materials comprise in general a metal oxide selected from the group consisting of zirconium dioxide, zinc oxide, aluminum oxide, silicon dioxide, titanium dioxide, magnesium oxide, lanthanum oxide, cerium oxide and mixtures thereof as ceramic support material. Preferred supports are zirconium dioxide and/or silicon dioxide; particular preference is given to mixtures of zirconium dioxide and silicon dioxide.

The active composition of the dehydrogenation catalyst material generally comprises one or more noble metals of transition group VIII, preferably platinum and/or palladium, particularly preferably platinum. In addition, the dehydrogenation catalyst can further comprise one or more elements of main groups I and/or II, preferably potassium and/or cesium. The dehydrogenation catalyst may also further comprise one or more elements of transition group III including the lanthanides and actinides, preferably lanthanum and/or cerium. Finally, the dehydrogenation catalyst can further comprise tin and preferably comprises tin.

In a preferred embodiment, the dehydrogenation catalyst comprises at least one element of transition group VIII, at least one element of main groups I and/or II, at least one element of transition group III including the lanthanides and actinides, and tin.

To produce the dehydrogenation catalyst support material which is applied as a washcoat layer on the monolith, it is possible to use precursors of oxides of zirconium, silicon, aluminum, titanium, magnesium, lanthanum or cerium which can be converted into the oxides by calcination. These can be produced by known methods, for example by the sol-gel process, precipitation of salts, dehydration of the corresponding acids, dry mixing, slurrying or spray drying. To produce a $ZrO_2.SiO_2$ mixed oxide, the zirconium-containing precursor obtained above can be mixed with a silicon-containing precursor. Well-suited precursors of $SiO_2$ are, for example, water-containing sols of $SiO_2$ such as Ludox™ or methoxyfunctional methyl polysiloxanes such as SILRES® MSE 100. The two components can be mixed, for example, by simple mechanical mixing or by spray drying in a spray dryer.

The ceramic catalyst support materials for the dehydrogenation catalysts which are applied as washcoat layers on the monoliths according to the present invention generally have high BET surface areas after calcination. The BET surface areas are generally greater than 40 m$^2$/g, preferably greater than 50 m$^2$/g, particularly preferably greater than 70 m$^2$/g. The pore volume of the dehydrogenation catalysts used according to the present invention is usually from 0.2 to 0.6 ml/g, preferably from 0.25 to 0.5 ml/g. The mean pore diameter of the dehydrogenation catalysts used according to the present invention, which can be determined by Hg porosimetry, is from 3 to 30 nm, preferably from 4 to 25 nm.

Furthermore, the dehydrogenation catalyst materials according to the present invention have a bimodal pore radius distribution. The pores have sizes in the range up to 20 nm and in the range from 40 to 5000 nm. These pores all together make up at least 70% of the total pore volume of the dehydrogenation catalyst. The proportion of pores smaller than 20 nm is generally in the range from 20 to 60%, while the proportion of pores in the range from 40 to 5000 nm is generally likewise from 20 to 60%.

The dehydrogenation-active component, which is a noble metal of transition group VIII, is generally applied by impregnation with a suitable metal salt precursor. Instead of impregnation, the dehydrogenation-active component can also be applied by other methods, for example spraying the metal salt precursor onto the support. Suitable metal salt precursors are, for example, the nitrates, acetates and chlorides of the corresponding metals; complex anions of the metals used are also possible. Preference is given to using platinum as $H_2PtCl_6$ or $Pt(NO_3)_2$. Suitable solvents for the metal salt precursors include both water and organic solvents. Particularly useful solvents are water and lower alcohols such as methanol and ethanol.

To apply alkali metals and alkaline earth metals, use is advantageously made of aqueous solutions of compounds which can be converted into the corresponding oxides by calcination. Suitable compounds are, for example, hydroxides, carbonates, oxalates, acetates or basic carbonates of the alkali metals and alkaline earth metals. If the catalyst support is doped with metals of main or transition group III, use is frequently made of the hydroxides, carbonates, nitrates, acetates, formates or oxalates which can be converted into the corresponding oxides by calcination, for example $La(OH)_3$, $La_2(CO_3)_2$, $La(NO_3)_3$, lanthanum acetate, lanthanum formate or lanthanum oxalate.

When using noble metals as dehydrogenation-active components, suitable precursors also include the corresponding noble metal sols which can be prepared by one of the known methods, for example by reduction of a metal salt using a reducing agent in the presence of a stabilizer such as PVP. The method of preparation is dealt with comprehensively in the German Patent Application DE 195 00 366.

The amount of a noble metal present as dehydrogenation-active component in the dehydrogenation catalysts used according to the present invention is from 0 to 5% by weight, preferably from 0.05 to 1% by weight, particularly preferably from 0.05 to 0.5% by weight.

The further components of the active composition can be applied either during production of the support, for example by coprecipitation, or subsequently, for example by impregnating the support with suitable precursor compounds. Precursor compounds used are generally compounds which can be converted into the corresponding oxides by calcination. Suitable precursors are, for example, hydroxides, carbonates, oxalates, acetates, chlorides or mixed hydroxycarbonates of the corresponding metals.

In advantageous embodiments, the active composition further comprises the following additional components:
at least one element of main group I or II, preferably cesium and/or potassium, in an amount of from 0 to 20% by weight, preferably from 0.1 to 15% by weight, particularly preferably from 0.1 to 10% by weight;
at least one element of transition group III including the lanthanides and actinides, preferably lanthanum and/or cerium, in an amount of from 0 to 20% by weight, preferably from 0.1 to 15% by weight, particularly preferably from 0.2 to 10% by weight;
tin in an amount of from 0 to 10% by weight.

The dehydrogenation catalyst is preferably halogen-free.

The calcination of the catalyst supports impregnated with the metal salt solution concerned is usually carried out at from 400 to 750° C., preferably from 500 to 700° C., particularly preferably from 550 to 650° C. for a period of from 0.5 to 6 hours.

Hydrogen Combustion Catalyst

A preferred catalyst which catalyzes the combustion of hydrogen comprises a noble metal of transition group VIII and/or I and/or of the periodic table and/or tin. Particularly preferred are catalysts containing platinum, optionally in combination with tin. As support materials for these catalysts a metal oxide selected from the group consisting of zirconium dioxide, zinc oxide, aluminum oxide, silicon dioxide, titanium dioxide, magnesium oxide, lanthanum oxide, cerium oxide, zeolites and mixtures thereof can be used. Preferred metal oxide supports are zirconium dioxide, magnesium oxide, silicon dioxide, zinc oxide and aluminum oxide or mixtures thereof.

The hydrogen catalyst may be used to selectively combust hydrogen in order to supply heat for a dehydrogenation as described above. In a further embodiment of the process the hydrogen combustion catalyst may also be used as a purification catalyst to selectively remove oxygen from hydrocarbon-containing streams.

Catalytic Dehydrogenation

The dehydrogenation can be performed as an oxidative or nonoxidative dehydrogenation. The nonoxidative dehydrogenation can be performed autothermally or non-autothermally. The dehydrogenation can be performed isothermally or adiabatically.

The nonoxidative catalytic alkane dehydrogenation is preferably performed autothermally. To this end, oxygen is additionally admixed to the reaction gas mixture of the dehydrogenation in at least one reaction zone, and the hydrogen and/or hydrocarbon present in the reaction gas mixture is combusted at least partly, which generates at least some of the heat of dehydrogenation required in the at least one reaction zone directly in the reaction gas mixture.

In a preferred embodiment, the inventive catalyst is used for the dehydrogenation of propane to propene or for the dehydrogenation of butane to butene.

One feature of the nonoxidative method compared to an oxidative method is the at least intermediate formation of hydrogen, which is manifested in the presence of hydrogen in the product gas of the dehydrogenation. In the oxidative dehydrogenation, no free hydrogen is found in the product gas of the dehydrogenation.

A suitable reactor form is the fixed bed tubular or tube bundle reactor. In these reactors, the catalyst (dehydrogenation catalyst and if appropriate a specialized oxidation catalyst) is disposed as a fixed bed in a reaction tube or in a bundle of reaction tubes. Customary reaction tube internal diameters are from about 10 to 15 cm. A typical dehydrogenation tube bundle reactor comprises from about 300 to 1000 reaction tubes. The internal temperature in the reaction tubes typically varies in the range from 300 to 1200° C., preferably in the range from 500 to 1000° C. The working pressure is customarily from 0.5 to 8 bar, frequently from 1 to 2 bar, when a low steam dilution is used, or else from 3 to 8 bar when a high steam dilution is used (corresponding to the steam active reforming process (STAR process) or the Linde process) for the dehydrogenation of propane or butane of Phillips Petroleum Co. Typical gas hourly space velocities (GHSV) are from 500 to 2000 $h^{-1}$, based on hydrocarbon used. The catalyst geometry may, for example, be spherical or cylindrical (hollow or solid). It is also possible to operate a plurality of fixed bed tubular reactors or tube bundle reactors alongside one another, of which at least one is alternately in the state of regeneration.

The nonoxidative catalytic, autothermal dehydrogenation may also be carried out under heterogeneous catalysis in a fluidized bed, according to the Snamprogetti/Yarsintez-FBD process. Appropriately, two fluidized beds are operated in parallel, of which one is generally in the state of regeneration. The working pressure is typically from 1 to 2 bar, the dehydrogenation temperature generally from 550 to 600° C. The heat required for the dehydrogenation can be introduced into the reaction system by preheating the dehydrogenation catalyst to the reaction temperature. The admixing of a cofeed comprising oxygen allows the preheater to be dispensed with and the required heat to be generated directly in the reactor system by combustion of hydrogen and/or hydrocarbons in the presence of oxygen. If appropriate, a cofeed comprising hydrogen may additionally be admixed.

The nonoxidative catalytic, autothermal dehydrogenation is preferably carried out in a tray reactor. This reactor comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by the reaction gas. In general, such a tray reactor is operated using a fixed catalyst bed. In the simplest case, the fixed catalyst beds are disposed axially in a shaft furnace reactor or in the annular gaps of concentric cylindrical grids. A shaft furnace reactor corresponds to one tray. The performance of the dehydrogenation in a single shaft furnace reactor corresponds to one embodiment. In a further, preferred embodiment, the dehydrogenation is carried out in a tray reactor having 3 catalyst beds.

In general, the amount of the oxygenous gas added to the reaction gas mixture is selected in such a way that the amount of heat required for the dehydrogenation of the alkane (e.g. propane and/or n-butane) is generated by the combustion of the hydrogen present in the reaction gas mixture and of any hydrocarbons present in the reaction gas mixture and/or of carbon present in the form of coke. In general, the total amount of oxygen supplied, based on the total amount of alkane, is from 0.001 to 0.5 mol/mol, preferably from 0.005 to 0.25 mol/mol, more preferably from 0.01 to 0.25 mol/mol. Oxygen may be used either in the form of pure oxygen or in the form of oxygenous gas which comprises inert gases. In order to prevent high alkane and alkene losses in the workup (see below), it may be advantageous when the oxygen content of the oxygenous gas used is high and is at least 50% by volume, preferably at least 80% by volume, more preferably at least 90% by volume. A particularly preferred oxygenous gas is oxygen of technical-grade purity with an $O_2$ content of approximately 99% by volume. In addition, a method is possible in which air is fed in as the oxygenous gas.

The hydrogen combusted to generate heat is the hydrogen formed in the catalytic alkane dehydrogenation and also any hydrogen additionally added to the reaction gas mixture as hydrogenous gas. The amount of hydrogen present should preferably be such that the molar $H_2/O_2$ ratio in the reaction gas mixture immediately after the oxygen is fed in is from 1 to 10 mol/mol, preferably from 2 to 6 mol/mol. In multistage reactors, this applies to every intermediate feed of oxygenous and any hydrogenous gas.

The hydrogen is combusted catalytically. The dehydrogenation catalyst used generally also catalyzes the combustion of the hydrocarbons and of hydrogen with oxygen, so that in principle no specialized oxidation catalyst is required apart from it. In one embodiment, operation is effected in the presence of one or more oxidation catalysts which selectively catalyze the combustion of hydrogen to oxygen in the presence of hydrocarbons. The combustion of these hydrocarbons with oxygen to give CO, $CO_2$ and water therefore proceeds only to a minor extent. The dehydrogenation catalyst and the oxidation catalyst are preferably present in different reaction zones.

When the reaction is carried out in more than one stage, the oxidation catalyst may be present only in one, in more than one or in all reaction zones.

Preference is given to disposing the catalyst which selectively catalyzes the oxidation of hydrogen at the points where there are higher partial oxygen pressures than at other points in the reactor, in particular near the feed point for the oxygenous gas. The oxygenous gas and/or hydrogenous gas may be fed in at one or more points in the reactor.

In one embodiment of the process according to the invention, there is intermediate feeding of oxygenous gas and of hydrogenous gas upstream of each tray of a tray reactor. In a further embodiment of the process according to the invention, oxygenous gas and hydrogenous gas are fed in upstream of each tray except the first tray. In one embodiment, a layer of a specialized oxidation catalyst is present downstream of every feed point, followed by a layer of the dehydrogenation catalyst. In a further embodiment, no specialized oxidation catalyst is present. The dehydrogenation temperature is generally from 400 to 1100° C.; the pressure in the last catalyst bed of the tray reactor is generally from 0.2 to 5 bar absolute, preferably from 1 to 3 bar absolute. The GHSV (gas hourly space velocity) is generally from 500 to 2000 $h^{-1}$, and, in high-load operation, even up to 100 000 $h^{-1}$, preferably from 4000 to 16 000 $h^{-1}$.

Catalytic Dehydrogenating Aromatization

The dehydrogenating aromatization is performed generally at temperatures of from 300 to 800° C., preferably from 400 to 700° C., more preferably from 450 to 650° C., and at pressures of from 100 mbar to 100 bar, preferably from 1 to 30 bar, more preferably from 1 to 10 bar, with an LHSV (Liquid Hourly Space Velocity) of from 0.01 to 100 $h^{-1}$, preferably from 0.1 to 20 $h^{-1}$. In addition to the hydrocarbon mixture, diluents such as $CO_2$, $N_2$, noble gases or steam may be present. It is likewise possible to add hydrogen if required, in which case the volume ratio of hydrogen to hydrocarbon (gases) may be from 0.1 to 100, preferably from 0.1 to 20. The hydrogen added, or that which has been formed in the dehydrogenation and, if appropriate, recycled, may be used to remove carbon which accumulates on the surface of the catalyst with increasing reaction time.

In addition to the continual (continuous) addition of a gas which prevents coke deposition during the reaction, there is the possibility of regenerating the catalyst from time to time by passing hydrogen or air over it. The regeneration itself takes place at temperatures in the range from 300 to 900° C., preferably from 400 to 800° C., with a free oxidizing agent, preferably with air or air-nitrogen mixtures, and/or in reducing atmosphere, preferably with hydrogen. The regeneration can be operated at atmospheric, reduced or superatmospheric pressure. Suitable pressures are, for example, from 500 mbar to 100 bar.

The invention is further illustrated by the following examples

EXAMPLES

Examples 1-12

Preparation of Inventive Dehydrogenation/Aromatization Catalysts by the a Process The A process describes the post impregnation of the active components after washcoating and calcining a monolithic honeycomb.

Washcoat Slurry Preparation

BASF SE zirconia spray dried powder D9-89 is used for washcoat slurry preparation. 17 000 g of this powder are dispersed in 15000 ml of water and mixed with 1200 g of SILRES® MSE 100. The resulting slurry with a theoretical total solid content of 52% has a pH of 3.2 to 3.8. This slurry is milled in a continuous mill for approximately 1 h to reach a final particle size of 11.5 μm on average with a tolerance band of +/−1.5 μm for 90% of the particles. The particle size distribution is controlled off-line multiply during the process by laser diffraction. The final slurry has again a pH of 3.2 to 3.8. The resulting slurry is used for coating.

Washcoating Process

This suspension is then properly diluted for coating the ceramic substrate at a total solid content of approximately 50% with a range of +/−1%. Coating was done by using an air ducted process. The right total solid content for the coating has to be determined in a targeting procedure to achieve the defined washcoat loading in g/in³ or g/L.

400 cpsi cordierite monolith parts from Corning Incorporated are used. For prototyping the parts are dipped to 80-90% into the slurry; after taking them out they are turned and the slurry drains through the cells. The washcoat loading is achieved by using the air gun to distribute the slurry across the channel and to blow out the excessive amount of slurry. The coating steps are repeated to finally reach the defined total washcoat loading of 4.5 g/in³. The prototypes are dried after each coating step at around 120 to 140° C. for 15 mins in a frequently reversing air flow and calcined at 560° C. for 3 h prior to the next step.

Impregnation of Active Components

The active components are applied in two steps by water uptake from solutions of the materials precursors. Initially, the water uptake of a representative sample is determined and the concentrations are calculated based on the uptake.

214.9 g of the MEA$_2$Pt(OH)$_6$ as 17.22% solution in MEA and 82 g of KOH are dissolved in 8000 g of water resulting in a pale yellow solution with a pH of around 12. The coated parts are drowned into the solution with a soaking time of 15 seconds. When taken out of the solution the parts are blown mildly with the above described air nozzle and dried in a reversing air flow at 120 to 140° C. for another 15 mins. Calcination takes place in a furnace or continuous calciner at 560° C. for approximately 3 h.

For the preparation of the second impregnation solution CsNO$_3$, SnCl$_2$.2H$_2$O and La(NO$_3$)$_3$ are dissolved in 6750 g of water taking the same water uptake into account for the wet impregnation. The parts are drowned and taken out of the solution after 15 seconds, blown free with a mild air flow. The parts are dried in a reversing air flow at 120 to 140° C. for another 15 mins. Calcination takes place in a furnace or continuous calciner at 560° C. for approximately 3 h.

Table 1 below shows an overview of the properties of the catalysts produced. The penetration depth ($d_{WC}$) was determined from the washcoat loading (WCL), the washcoat density ($\rho_{WC}$) and the geometric surface area (GSA) of the monolith:

$$d_{WC} = \frac{WCL/\rho_{WC}}{GSA}$$

The washcoat density ($\rho_{WC}$) was determined from the densities of the finished monolith catalyst ($\rho_{catalyst}$) and of the cordierite substrate ($\rho_{substrate}$), and the washcoat loading and the specific weight (SW: volume-based total weight of the catalyst) of the monolith catalyst:

$$\rho_{WC} = \frac{WCL}{SW/\rho_{catalyst} - (SW - WC)/\rho_{substrate}}$$

The densities of the monolith catalyst and of the cordierite substrate were determined by means of mercury or helium density measurements.

TABLE 1

| Ex. | Wash-coat loading [g/l] | Spec. weight [g/l] | Pt loading [g/l] | Elemental composition [% by wt.] | | | | | | | Penetration depth [μm] |
|---|---|---|---|---|---|---|---|---|---|---|---|
| | | | | Pt | Sn | K | Cs | La | Zr | Si | |
| 1 | 320 | 652 | 2.0 | 0.31 | 0.88 | 0.06 | 0.21 | 1.2 | 29 | 13 | 153 |
| 2 | 320 | 623 | 1.5 | 0.24 | 0.56 | 0.16 | 0.26 | 2.7 | 32 | 11 | 148 |
| 3 | 320 | 623 | 1.4 | 0.22 | 0.51 | 0.18 | 0.24 | 2.6 | 31 | 12 | 148 |
| 4 | 320 | 623 | 1.3 | 0.21 | 0.55 | 0.15 | 0.25 | 2.5 | 30 | 12 | 148 |
| 5 | 320 | 623 | 1.7 | 0.27 | 0.53 | 0.17 | 0.23 | 2.4 | 27 | 13 | 148 |
| 6 | 320 | 623 | 1.5 | 0.24 | 0.51 | 0.17 | 0.24 | 2.5 | 29 | 13 | 148 |
| 7 | 320 | 623 | 1.6 | 0.25 | 0.57 | 0.15 | 0.21 | 2.3 | 25 | 14 | 148 |
| 8 | 320 | 623 | 1.9 | 0.31 | 0.45 | 0.15 | 0.21 | 2.4 | 30 | 12 | 148 |
| 9 | 320 | 623 | 1.9 | 0.3 | 0.53 | 0.16 | 0.16 | 2.6 | 28 | 13 | 148 |
| 10 | 300 | 638 | 0.9 | 0.14 | 0.48 | 0.19 | 0.23 | 1.3 | 30 | 13 | 143 |
| 11 | 290 | 602 | 2.0 | 0.34 | 0.44 | 0.2 | 0.23 | 2.55 | 31 | 12 | 135 |
| 12 | 280 | 717 | 0.5 | 0.064 | 0.26 | 0.13 | 0.19 | 1.9 | 22 | 15 | 138 |

Example 13

Preparation of Inventive Dehydrogenation/Aromatization Catalysts by the B Process The B process differs just slightly from the A process here, the active components are already impregnated into the support material and milled to form a suspension prior to coating onto the monolith substrate.

Washcoat Slurry Preparation and Active Component Impregnation 6220 g of Zirconia D9-89 are impregnated with 131.4 g of a solution of the Pt salt used in examples 1 to 12 and 23 g KOH diluted in 1730 g of water. This impregnated Zirconia is subsequently impregnated with a solution of 45 g SnCl$_2$.2H$_2$O, 35 g CsNO3 and 237 g La(NO$_3$)$_3$ dissolved in 3270 g of water containing 13 g of HCl (37%). The resulting suspension is milled at the pH of 3.6 in a continuous mill for approximately 1 h to reach a final particle size of 10.5 µm on average (with a tolerance band of +/−1.5 µm for 90% of the particles). The particle size distribution is controlled several times off-line during the process by laser diffraction. The final slurry has a pH of 3.6 to 4. The resulting slurry is used for coating.

Washcoating Process

The coating is performed as described above in 3 separate steps followed by drying at around 130° C. and calcining at 590° C. after each of the coating steps.

Table 2 below shows an overview of the properties of the example catalyst produced. The penetration depth was determined as described in examples 1 to 12.

TABLE 2

| Ex. I | Wash-coat loading [g/l] | Spec. weight [g/l] | Pt loading [g/l] | Elemental composition [% by weight] | | | | | | | Penetration depth [µm] |
|---|---|---|---|---|---|---|---|---|---|---|---|
| | | | | Pt | Sn | K | Cs | La | Zr | Si | |
| 13 | 270 | 697 | 0.8 | 0.11 | 0.22 | 0.09 | 0.17 | 1.1 | 24 | 15 | 133 |

Comparative Example 1

Preparation of Extrudate Catalysts for Dehydrogenation/Aromatization

The catalyst was produced in extrudate form according to example 4 of DE 199 37 107.

The Pt loading of this catalyst was 4.0 g/l.

Propane Dehydrogenation on the Laboratory Scale

Examples 14 to 19 and Comparative Examples 2 to 5

General Procedure

The reactors consist of an inner tube made of 1.4841 steel surrounded by insulating material and an outer pressure casing made of 1.4541 steel. The reactor is designed for an adiabatic method. The pressure casing itself has support heating by a heating belt in order to compensate for heat losses from the inner tube. The inner tube has an internal diameter of 20 mm. The catalyst is filled into this inner tube. Above the adiabatic region, in the upper third (upstream in relation to the catalyst), there is a copper-jacketed preheater.

Propane, nitrogen, hydrogen and air were metered into the reactor in gaseous form by means of mass flow regulators (from Brooks). The air was added separately through an 8 cm lance upstream of the catalyst bed. Water was conveyed from a reservoir vessel by means of an HPLC pump into a steel tube evaporator, and the steam raised was conducted with heating into the reactor.

The exit gases were introduced via a pressure regulator and a filter into a water separator cooled to 10° C. Downstream of the separator, the exit gas was passed via a downstream pressure regulator at approx. 1.3 bar (abs) into an online gas chromatograph (HP5890, from Agilent) for analysis and determination of the conversions and selectivities.

To perform the propane dehydrogenation, the catalyst was installed into the middle of the adiabatic section of the reactor. The inventive catalysts were in each case a round honeycomb core of length 101.6 mm and diameter 15 mm. In the case of the comparative catalysts, 20 ml of 1.5 mm extrudate were installed. Upstream and downstream of the catalyst bed, inert material (2-3 mm steatite spheres) was installed.

For the first activation, the catalyst was reduced with a hydrogen stream (of 12 l (STP)/h) at 450° C. and 3 bar (abs) for 45 minutes. During the dehydrogenation, the preheater temperature was set to 450° C. and the reaction pressure was 1.5 bar (abs). The dehydrogenation was performed autothermally, i.e. with simultaneous combustion of hydrogen in order to provide the heat of dehydrogenation needed. The dehydrogenation cycle length was 12 h.

Between the dehydrogenation cycles, the catalyst was regenerated by coke burnoff and subsequent reduction with hydrogen. The coke was burnt off initially at preheater temperature of 450° C. and 3 bar (abs) with lean air (nitrogen/air mixture, air flow 15 l (STP)/h with oxygen content 1% by volume. Thereafter, the air content was increased gradually up to 100% (air flow 80 l (STP)/h) and the temperature was increased to 550° C. The hydrogen reduction was performed at 450° C., 3 bar (abs) and with 12 l (STP)/h of hydrogen.

Table 3 below shows results of the autothermal propane dehydrogenation at a load (Gas Hourly Space Velocity, GHSV) of 2000 l (STP) (propane)/l (catalyst)/h. The feed gas mixture composition was 41.0% by volume of propane, 41.0% by volume of water, 5.1% by volume of hydrogen, 10.3% by volume of nitrogen and 2.6% by volume of oxygen. The values reported are average values of three dehydrogenation cycles of the fresh catalyst. It becomes clear from this that the inventive catalysts (from examples 8, 12 and 13) achieve significantly higher Pt-based propene space-time yields than extrudate catalysts according to the prior art. This is true of catalysts produced both by the A process (examples 1 to 12) and by the B process (example 13).

TABLE 3

| Catalyst from example | Form | Conversion [%] | Selectivity [%] | Space-time yield [$kg_{propene}/kg_{Pt}/h$] |
|---|---|---|---|---|
| 8 | honeycomb | 17 | 97 | 295 |
| 12 | honeycomb | 11 | 96 | 831 |
| 13 | honeycomb | 10 | 97 | 486 |
| comparative 1 | bed | 18 | 96 | 159 |

Table 4 below shows results of the autothermal propane dehydrogenation at different loads (GHSV) of 1000 to 6000 $l_{propane}$ (STP)/$l_{catalyst}$/h and a feed composition of 42.6% by volume of propane, 42.6% by volume of water, 4.2% by volume of hydrogen, 8.5% by volume of nitrogen and 2.1% by volume of oxygen. The values are average values from three cycles of a catalyst formed over 35 cycles. It becomes clear from this that the inventive catalyst (example 10), even after long run time and at different loads, achieves significantly higher Pt-based propene space-time yields than extrudate catalysts according to the prior art.

TABLE 4

| Catalyst from example | Form | GHSV [h$^{-1}$] | Conversion [%] | Selectivity [%] | Space-time yield [kg$_{propene}$/kg$_{Pt}$/h] |
|---|---|---|---|---|---|
| 10 | honeycomb | 2000 | 13 | 98 | 525 |
| comparative 1 | bed | 2000 | 15 | 99 | 137 |
| 10 | honeycomb | 4000 | 11 | 98 | 910 |
| comparative 1 | bed | 4000 | 13 | 99 | 235 |
| 10 | honeycomb | 6000 | 10 | 98 | 1209 |
| comparative 1 | bed | 6000 | 10 | 98 | 283 |

Propane Dehydrogenation on the Pilot Scale

The tests of propane dehydrogenation were conducted in a stainless steel adiabatic reactor (steel 1.4841, 36 mm inner diameter, 4 m length) which consists of 3 catalyst beds of approximately 90 cm long each depending on the type of catalyst. The temperature throughout the catalyst bed were monitored by two 14-point thermal elements (6 mm ID) inserted through the middle of the catalyst bed, one from the top and one from the bottom. The reaction consists of a mixture of propane, hydrogen, steam, and pure $O_2$. $O_2$ and steam were introduced as a mixture at three separate dosing points, one prior to each catalyst. The distance between the dosing points from the catalyst bed varied but in general between 55 and 150 mm. Furthermore, the $O_2$ flow rates were slowly ramped up over the course of a dehydrogenation cycle while holding the feed rates of the other components constant. Prior to entering the reactor, the mixture of hydrogen and propane were preheated by passing through separate preheaters at 520, 525, 530, 580° C.

When testing was performed with catalyst in extrudate form, 3 mm extrudate catalyst from comparative example 1 was used. When testing was performed with monolith catalyst the catalyst from example 11 was used. A total of 6 monoliths (34 mm D×15 cm L) were stacked together to form one bed. In the centre of each monolith an opening of 6 mm along the axis direction was drilled to allow thermolements to fit through. The perimeters of the top and the bottom of a monolith were sealed with glass fiber to prevent flow bypass. In each case, a layer of steatite was filled in between two catalyst beds.

The activity tests were performed continuously, alternating between dehydrogenation and regeneration cycles (approximately 10 hours each). After each dehydrogenation cycle, the reactor was flushed with $N_2$. The regeneration procedure was started at 4.5 bar with a diluted air mixture for 240 min, followed pure air for 8 hours. At the end of the regeneration cycle, a total of 6 pressure-release cycles (alternating between 0.5 and 4 bar, each 10 min) were conducted to remove the remaining trace of coke on the surface. After flushing the reactor in $N_2$, the catalyst was reduced, starting with diluted $H_2$ for 30 min followed by pure $H_2$ for 30 min at 500° C. Subsequently the reaction feed was again introduced into the reactor for the next dehydrogenation cycle.

The conversion and selectivity reported for each cycle are the average over the cycle. The space velocity is defined as propane feed rate/volume of catalyst, in which volume of catalyst is defined as the volume of the bed occupied by catalyst, including void volume.

Example 20

A total of 18 monoliths from example 11 with a total weight of 1448 g (2.30 l) was equally distributed in three beds. Each bed consisted of 6 monoliths, and the Pt content was 2.0 g Pt/L reactor volume. 6360 g/h propane (GHSV$_{C3}$=1400 L$_{C3}$/L$_{cat}$/h) and 75 g/h $H_2$ were fed into the reactor as reaction mixture with $O_2$ and $H_2O$ (steam) fed at each feeding point. The steam was fed at a rate of 1000 g/h at each feeding point while the $O_2$ rate was varied throughout the cycle in the order according to table 5 hereinbelow:

TABLE 5

| dehydrogenation time (min) | $O_2$ 1$^{st}$ feeding point (g/h) | $O_2$ 2$^{nd}$ feeding point (g/h) | $O_2$ 3$^{rd}$ feeding point (g/h) |
|---|---|---|---|
| 25 | 0 | 0 | 0 |
| 26 | 30 | 30 | 30 |
| 27 | 80 | 40 | 40 |
| 28 | 135 | 60 | 50 |
| 29 | 210 | 85 | 60 |
| 30 | 250 | 110 | 75 |
| 31 | 280 | 125 | 80 |
| 69 | 340 | 131 | 85 |
| 107 | 340 | 134 | 86 |
| 144 | 340 | 137 | 87 |
| 182 | 340 | 140 | 88 |
| 220 | 340 | 143 | 89 |
| 258 | 340 | 147 | 90 |
| 295 | 340 | 151 | 92 |
| 333 | 340 | 155 | 94 |
| 371 | 340 | 160 | 96 |
| 409 | 340 | 165 | 100 |
| 446 | 340 | 170 | 105 |
| 484 | 340 | 175 | 110 |
| 522 | 330 | 185 | 120 |
| 560 | 325 | 195 | 120 |
| 598 | 320 | 200 | 132 |
| 635 | 315 | 205 | 137 |

The average propane conversion and propylene selectivity over the cycle are 35% and 95%, respectively, with a space time yield of 420 kg$_{propylene}$/kg$_{Pt}$/h.

Example 21

All conditions remained the same as in example 20 but with 8600 g/h of propane and the $O_2$ feed according to table 6 hereinbelow:

TABLE 6

| dehydrogenation time (min) | $O_2$ 1$^{st}$ feeding point (g/h) | $O_2$ 2$^{nd}$ feeding point (g/h) | $O_2$ 3$^{rd}$ feeding point (g/h) |
|---|---|---|---|
| 10 | 0 | 0 | 0 |
| 13 | 250 | 135 | 105 |
| 16 | 275 | 150 | 111 |
| 54 | 278 | 161 | 121 |
| 92 | 280 | 163 | 123 |
| 129 | 283 | 164 | 123 |
| 167 | 285 | 164 | 124 |
| 205 | 287 | 165 | 124 |
| 243 | 288 | 165 | 124 |
| 280 | 289 | 166 | 124 |
| 318 | 290 | 166 | 124 |
| 356 | 291 | 167 | 124 |
| 394 | 292 | 167 | 125 |
| 431 | 293 | 168 | 125 |
| 469 | 294 | 168 | 125 |
| 507 | 295 | 168 | 125 |
| 545 | 295 | 168 | 126 |
| 583 | 295 | 170 | 126 |
| 620 | 295 | 170 | 126 |

The average propane conversion and propylene selectivity over the cycle were 28% and 95%, respectively, with a space time yield of 446 kg(propene)/kg(Pt)/h.

Comparative Example 6

A total of 3.27 kg (2.49 L) 3 mm extrudates was equally distributed in three beds. Each bed consisted of 1090 g catalyst (830 ml) catalysts. The Pt loading was 4.0 $g_{Pt}$/L reactor volume. 6360 g/h propane ($GHSV_{C3}$=1300 $L_{C3}/L_{cat}$/h) and 75 g/h $H_2$ were fed into the reactor as reaction mixture with $O_2$ and $H_2O$ fed at each feeding point. The steam was fed at a rate of 1000 g/h at each feeding point while the $O_2$ rate was varied throughout the cycle in the order according to table 7 hereinbelow:

TABLE 7

| Dehydrogenation time (min) | $O_2$ 1st feeding point (g/h) | $O_2$ 2nd feeding point (g/h) | $O_2$ 3rd feeding point (g/h) |
|---|---|---|---|
| 3 | 235 | 160 | 40 |
| 6 | 250 | 195 | 55 |
| 44 | 260 | 197 | 65 |
| 82 | 265 | 200 | 67 |
| 119 | 267 | 205 | 69 |
| 157 | 269 | 210 | 71 |
| 195 | 271 | 212 | 73 |
| 233 | 273 | 214 | 75 |
| 270 | 275 | 216 | 80 |
| 308 | 276 | 218 | 85 |
| 346 | 277 | 220 | 87 |
| 384 | 278 | 222 | 89 |
| 421 | 279 | 224 | 91 |
| 459 | 280 | 226 | 93 |
| 497 | 280 | 228 | 95 |
| 535 | 280 | 230 | 95 |
| 573 | 280 | 230 | 95 |
| 610 | 280 | 230 | 95 |

The average propane conversion and propylene selectivity over the cycle are 35% and 95%, respectively, with a space time yield of 210 kg(propylene)/kg(Pt)/h.

Comparative Example 7

All conditions remained the same as in comparative example 7 but with 8600 g/h of propane and the $O_2$ feed according to table 8 hereinbelow:

| Dehydrogenation time (min) | $O_2$ 1st feeding point (g/h) | $O_2$ 2nd feeding point (g/h) | $O_2$ 3rd feeding point (g/h) |
|---|---|---|---|
| 3 | 245 | 155 | 50 |
| 6 | 260 | 190 | 65 |
| 44 | 270 | 192 | 75 |
| 82 | 275 | 195 | 77 |
| 119 | 277 | 200 | 79 |
| 157 | 279 | 205 | 81 |
| 195 | 281 | 207 | 83 |
| 233 | 283 | 209 | 85 |
| 270 | 285 | 211 | 90 |
| 308 | 286 | 213 | 95 |
| 346 | 287 | 215 | 97 |
| 384 | 288 | 217 | 99 |
| 421 | 289 | 219 | 101 |
| 459 | 290 | 221 | 103 |
| 497 | 290 | 223 | 105 |
| 535 | 292 | 225 | 107 |
| 573 | 292 | 225 | 107 |
| 610 | 292 | 225 | 107 |

The average propane conversion and propylene selectivity over the cycle are 29% and 96%, respectively, with a space time yield of 242 kg(propylene)/kg(Pt)/h.

n-Butane Dehydrogenation on the Laboratory Scale

Example 22 and Comparative Example 8

The n-butane dehydrogenation was performed in an electrically heated tubular reactor (1.4841 steel, internal diameter 18 mm). n-Butane, nitrogen, hydrogen and air were metered into the reactor in gaseous form by means of mass flow regulators. The air was added separately via a lance 10 cm upstream of the catalyst bed. Water was conveyed from a reservoir vessel via an HPLC pump into a steel tube evaporator, and the water vapor which formed was conducted into the reactor.

The exit gases were introduced via a pressure regulator into a water separator cooled to 10° C. Downstream of the separator, the exit gas was passed into an online gas chromatograph (µGC, from Varian) for analysis and determination of the conversions and selectivities.

To perform the n-butane dehydrogenation, the catalyst was installed into the middle of the isothermal section of the reactor. In the case of the inventive catalyst, a round honeycomb core of length 101.6 mm and of diameter 15 mm was installed. In the case of the comparative catalyst, 20 ml of 1.5 mm extrudate were installed. Upstream and downstream of the catalyst bed, inert material (2-3 mm steatite spheres) was introduced.

For first activation, the catalyst was reduced with a hydrogen stream of 10 l (STP)/h at 500° C. and 2.5 bar (abs) for 30 minutes. During the dehydrogenation, the reactor oven temperature was set to 570° C. The reaction pressure was 1.5 bar (abs). The dehydrogenation cycle length was 12 h. The dehydrogenation was performed at a load (Gas Hourly Space Velocity, GHSV) of 500 l (STP) (n-butane)/l (catalyst)/h and with the following feed gas mixture composition: 41.4% by volume of n-butane, 16.6% by volume of water, 18.6% by volume of hydrogen, 18.7% by volume of nitrogen and 4.7% by volume of oxygen.

Between the cycles, the catalyst was regenerated by coke burnoff and subsequent reduction with hydrogen at 2.5 bar (abs). The coke was initially burnt off with lean air (nitrogen/air mixture, air flow 5 l (STP)/h with oxygen content 4% by volume at oven temperature 400° C. Thereafter, the air content was increased gradually to 100% (air flow 33 l (STP)/h) and the temperature was increased to 500° C. In the course of reduction over 30 min, the temperature was 500° C. and the hydrogen flow was 10 l (STP)/h.

Table 9 below shows the average values from three cycles of catalysts formed over at least 20 cycles. In the case of butane dehydrogenation too, it becomes clear that the inventive catalyst from example 8, with similar conversion and similar selectivity, achieves a significantly higher platinum-based space-time yield than extrudate catalysts according to the prior art.

TABLE 9

| Catalyst from example | Form | Conversion [%] | Selectivity [%] | Space-time yield [$kg_{butene}/kg_{Pt}$/h] |
|---|---|---|---|---|
| comparative 1 | bed | 40 | 95 | 120 |
| 8 | honeycomb | 38 | 96 | 230 |

Example 23 n-Butane Dehydrogenation on the Pilot Scale

The reactors consist of a steel inner tube made of 1.4841 steel, which is surrounded by insulating material and an outer pressure casing made of 1.4541 steel. The reactor is designed for an adiabatic method. The pressure casing itself has support heating by a heating collar in order to compensate for heat losses from the inner tube. The inner tube has an internal diameter of 52.5 mm and a length of 2.25 m. Catalyst is filled into this inner tube. Upstream in relation to the adiabatic reactor there is a steel preheater heated with a heating collar.

n-Butane, nitrogen, hydrogen, oxygen and air were metered into the reactor in gaseous form via mass flow regulators. Oxygen for the dehydrogenation was added separately via lances 25 cm upstream of the catalyst bed. Water was likewise conveyed into steel tube evaporators in liquid form via mass flow regulators, and the water vapor which formed was conducted into the reactor in heated form.

The exit gases were introduced via a pressure regulator and a filter into a water separator cooled to 10° C. Downstream of the separator, the exit gas was passed into an online gas chromatograph (HP5890, from Agilent) for analysis and determination of the conversions and selectivities.

To perform the n-butane dehydrogenation, the catalyst was installed in three catalyst beds in the adiabatic section of the reactor, each separated from one another by an inert bed of steatite (rings, height×external diameter×internal diameter=5×3×2 mm). The total catalyst volume installed was 1 l; this was divided into three catalyst beds of the same volume. In the case of the inventive catalyst, honeycomb cores of diameter 5 cm and adjusted lengths were installed. In the case of the comparative catalyst, 3.0 mm extrudate was used.

For the first activation, the catalyst was reduced with a hydrogen flow of 200 l (STP)/h at 500° C. and 2.5 bar (abs) for 45 minutes. In the course of dehydrogenation, the preheater temperature was set to 450° C. and the reaction pressure was 2.25 bar (abs). The dehydrogenation was performed autothermally, i.e. with simultaneous combustion of hydrogen in order to provide the necessary heat of dehydrogenation. The dehydrogenation cycle length was 12 h.

The dehydrogenation was performed at a load (Gas Hourly Space Velocity, GHSV) of 650 l (STP) (n-butane)/l (catalyst)/h (1.7 kg/h of n-butane) and with the following feed gas mixture composition: 35% by volume of n-butane, 41% by volume of water, 16% by volume of hydrogen, 2.7% by volume of nitrogen and 5.3% by volume of oxygen. Oxygen was fed in fractions upstream of the catalyst beds: 40% upstream of the first bed in flow direction, 35% upstream of the second bed and 25% upstream of the third bed. During the dehydrogenation, the preheater temperature was set to 470° C. At a dehydrogenation cycle length of 12 h, the reaction pressure was 1.5 bar (abs).

Between the dehydrogenation cycles, the catalyst was regenerated by coke burnoff and subsequent reduction with hydrogen. The coke was initially burnt off at preheater temperature 450° C. and 4.8 bar (abs) with lean air with oxygen content 1% by volume (nitrogen/air mixture, air flow 250 l (STP)/h). Thereafter, the air content was increased gradually up to 100% (air flow 1500 l (STP)/h) and the temperature was increased to 500° C. The hydrogen reduction was performed at 500° C., 2.5 bar (abs) and with 200 l (STP)/h of hydrogen.

Table 10 below shows the average values from three cycles of formed catalysts. In the butane dehydrogenation on the pilot scale too, it becomes clear that the inventive catalyst (PDR7927), with similar conversion and similar selectivity, achieves a significantly higher Pt-based butene space-time yield than bulk catalysts according to the prior art.

TABLE 10

| Catalyst from example | Form | Conversion [%] | Selectivity [%] | Space-time yield [$kg_{butene}/kg_{Pt}/h$] |
|---|---|---|---|---|
| comparative 1 | bed | 40 | 95 | 158 |
| examples 2-9 | honeycomb | 41 | 95 | 398 |

Examples 24 and 25

The dehydrogenating aromatization was performed in an electrically heated tubular reactor (1.4841 steel, internal diameter 21 mm). 20 ml of extrudate catalyst from comparative example 1 or 12 ml of catalyst from example 1 were installed into the reactor and activated with hydrogen at 400° C. for 1 h. The feed stocks metered into the reactor were hydrogen, water and a $C_8$ fraction with approx. 95% by weight of o-xylene precursors, principally 3,4- and 2,3-dimethyl-2-hexene ("DMH" for short). Hydrogen was metered into the reactor in gaseous form via a mass flow regulator. Water and the C8 fraction were conveyed from a reservoir vessel by means of HPLC pumps into a steel tube evaporator, and the gas mixture which formed was conducted into the reactor in heated form. The dehydrogenating aromatization was performed at oven temperature 400° C., 1 bar (abs), 14 g/h of organic components, $H_2O$/DMH 16/1 mol/mol and $H_2$/DMH 3/1 mol/mol.

Table 11 below shows average results of the aromatization over 4 hours of run time. Likewise in the aromatization to o-xylene, it comes clear that the inventive catalyst (PDR6936), with similar conversion, achieves a significantly higher Pt-based o-xylene space-time yield than extrudate catalysts according to the prior art.

TABLE 11

| Catalyst from example | Form | DMH conversion [%] | Xylene selectivity | o-Xylene (m-xylene + p-xylene) ratio | Space-time yield [$kg_{o-xylene}/kg_{Pt}/h$] |
|---|---|---|---|---|---|
| 1 | honeycomb | 50 | 19 | 17 | 58 |
| comparative 1 | bed | 54 | 38 | 9 | 37 |

Example 25

Preparation of Catalyst for Selective Combustion of Hydrogen with Oxygen in the Presence of Hydrocarbons Incipient Wetness Impregnation Procedure for Pt/Sn on alpha $Al_2O_3$ Support 2-4 mm alpha aluminium oxide spheres from Axens (Alumina Spheralite 512) were used as support material. The impregnation procedure was as follows:
i To determine the incipient wetness of the alumina material which is to be impregnated,
   a) 10 g of the alumina support material was placed in a plastic vial.
   b) Deionized water (DI water) was added to the material in increments of 10% of the total weight of the support.

c) The water and the support were mixed together. When the point of incipient wetness was reached, the support material clumped together.

d) For the 10 g alumina sample a total of 4 g of water was added. The weight percentage of water to be added to the support was determined to be 40 wt.-%.

ii The amount of Pt nitrate solution needed to obtain the Pt level desired was determined. For 50 g of alumina support material 0.52 g of Pt nitrate solution with a concentration of 13.46% Pt nitrate were diluted to 20 ml of solution and added.

iii The liquid was poured into the dry powder. The two components were mixed until the mixture was homogenous.

iv The mixture was dried at 75° C. for 16 hours.

v The desired amount of $SnCl_2.2H_2O$ needed was calculated and dissolved in DI water. For 50 g of alumina support material 0.046 g of tin chloride solid were dissolved in 20 ml of water and added.

vi The mixture was dried at 75° C. for 16 hours.

vii Calcination was carried out at 540° C. for 2 hours.

Washcoating Procedure for Coating the Pt/Sn Frit onto a Monolith Substrate

The workcoaching procedure was as follows:

i Milling or reducing the particle size of the frit.

a) A 35% solids content slurry using the Pt/Sn on alumina support and DI water was prepared.

b) The slurry was placed in a mini ceramic ball-mill.

c) The ball-mill was placed on a US Stoneware roller and the speed controller set to about 107 rpms.

d) Milling was carried out for about 9 hours until 90% of particles become smaller than 10 μm.

ii The slurry was emptied into a storage container.

iii Cores were cut from a piece of Corning, 400 cpsi/6.5 mil block of blank substrate. The cores are 16 mm in diameter and 100 mm long. The total volume was 324 ml.

iv The slurry was mixed until it was uniform. Then the jar was emptied into a cylinder that was a little bigger in diameter than the core. The core was submerged into the slurry and removed after about 5 seconds. The excess slurry was shaken off from the core and the channels were blown clear.

v The mixture was dried at 75 to 90° C. for 16 hours.

vi Steps iv and v were repeated until the dried washcoat was between 0.16 to 0.17 g/ml.

vii Calcination was carried out at 540° C. for 2 hours, viii The mass of the core is determined when the core was above 150° C. By weighing the core warm, a correct weight of the washcoat loading can be determined. As the core cools, it will take up water which will result in an incorrect washcoat loading.

The characteristics of the prepared catalyst are given in the 12 below. The penetration depth was determined as described in examples 1 to 12.

TABLE 5

| Example | Washcoat loading [g/l] | Spec. weight [g/l] | PT loading [g/l] | Elemental composition [% by wt.] | | | Penetration depth [μm] |
|---|---|---|---|---|---|---|---|
| | | | | Pt | Sn | Al | |
| 25 | 166 | 485 | 0.16 | 0.033 | 0.031 | 32 | 64 |

Comparative Example 9

Preparation of Bulk Catalyst for Selective $O_2$ Combustion with Hydrogen

The catalyst was prepared according to WO 2005097715, example A.

Example 26 and Comparative Example 10

Oxygen Removal by Catalytic Combustion with Hydrogen on the Laboratory Scale

The selective catalytic $O_2$ combustion was performed in an electrically heated tubular reactor (1.4841 steel, internal diameter 18 mm). n-Butane, 1,3-butadiene, nitrogen, hydrogen and air were metered into the reactor in gaseous form via mass flow regulators (from Bronckhorst). Water was conveyed from a reservoir vessel by means of an HPLC pump into a steel tube evaporator, and the water vapor which formed was conducted into the reactor.

The exit gases were introduced via a pressure regulator into a water separator cooled to 10° C. Downstream of the separator, the exit gas was passed into an online gas chromatograph (μGC, from Varian) for analysis and determination of the conversions and selectivities.

To perform the $O_2$ removal, the catalyst was installed into the middle of the isothermal section of the reactor. In the case of the inventive catalyst, a round honeycomb core of length 101.6 mm and of diameter 15 mm was installed. In the case of the comparative catalyst, 20 ml of 1.5 mm extrudate were installed. Upstream and downstream of the catalyst bed, there was a bed of inert material (2-3 mm steatite spheres).

During the $O_2$ combustion, the reactor oven temperature was set to 300° C. The reaction pressure was 1.5 bar (abs). The $O_2$ combustion was performed with a C4 feed stream of 20 l $(STP)_{C4}$/h and with the following feed gas mixture composition: 11.6% by volume of n-butane, 9.8% of 1,3-butadiene, 23.5% by volume of water, 6.2% by volume of hydrogen, 47.0% by volume of nitrogen and 1.9% by volume of oxygen.

Table 12 below shows results of the catalytic oxygen removal after 2 days of run time. In the selective $O_2$ combustion with hydrogen, it becomes clear that the inventive catalyst, at a significantly higher Pt-based oxygen load (WHSV, Weight Hourly Space Velocity), achieves a similar $O_2$ conversion to that for bulk catalysts according to the prior art.

TABLE 13

| Catalyst from example | Form | $O_2$ WHSV [$kg_{O2}/kg_{Pt}$/h] | $O_2$ conversion | $H_2$ combustion selectivity |
|---|---|---|---|---|
| 25 | honeycomb | 1181 | 99.7 | 90 |
| comparative 9 | bed | 91 | 99.7 | 90 |

The invention claimed is:

1. A process for dehydrogenating alkanes to alkenes comprising contacting in a reaction zone an alkane containing reaction gas mixture with a catalyst comprising a monolith composed of a catalytically inert material with a BET surface area of <10 m²/g and a catalyst layer which has been applied to the monolith and comprises, on an oxidic support material, at least one noble metal selected from the group consisting of the noble metals of group VIII of the Periodic Table of the Elements, optionally tin and/or rhenium, and optionally further metals, wherein catalyst layer has a thickness of 5 to 500 micrometers, wherein the dehydrogenation is performed as a nonoxidative dehydrogenation performed autothermally, wherein the gas hourly space velocity is from 500 to 2,000 $h^{-1}$.

2. The process according to claim 1, wherein the catalyst layer comprises a further metal which is selected from the third transition group of the Periodic Table of the Elements including the lanthanides and/or an alkali metal or alkaline earth metal.

3. The process according to claim 1, wherein the at least one noble metal of group VIII of the Periodic Table of the Elements is platinum.

4. The process according to claim 1, wherein the oxidic support material is selected from the group consisting of oxides of magnesium, calcium, aluminum, silicon, titanium and zirconium.

5. The process according to claim 1, wherein the catalyst comprises a monolith of cordierite.

6. The process according to claim 1 wherein the alkane is propane and the alkene is propene or the alkane is n-butane and the alkene is butenes.

7. The process according to claim 1, wherein the autothermal dehydrogenation is carried out in a tray reactor.

8. The process according to claim 1, wherein the catalyst also catalyzes the combustion of hydrocarbons and of hydrogen present in the reaction gas mixture.

9. A process for dehydrogenating aromatization comprising contacting in a reaction zone a hydrocarbon containing reaction gas mixture with a catalyst comprising a monolith composed of a catalytically inert material with a BET surface area of <10 $m^2/g$ and a catalyst layer which has been applied to the monolith and comprises, on an oxidic support material, at least one noble metal selected from the group consisting of the noble metals of group VIII of the Periodic Table of the Elements, optionally tin and/or rhenium, and optionally further metals, wherein the catalyst layer has a thickness of 5 to 500 micrometers, wherein the dehydrogenating aromatization is performed at temperatures of from 300 to 800° C.; wherein the liquid hourly space velocity is from 0.01 to 20 $h^{-1}$.

10. The process according to claim 9, wherein hydrogen is added to the hydrocarbon containing reaction gas mixture.

11. The process according to claim 10, wherein the volume ratio of hydrogen to hydrocarbon is from 0.1 to 100.

12. The process according to claim 1, wherein the catalyst layer comprises at least one of the elements selected from the group consisting of tin, lanthanum, and combinations thereof.

* * * * *